(12) United States Patent
Black et al.

(10) Patent No.: US 11,000,819 B2
(45) Date of Patent: May 11, 2021

(54) GUARD BED SYSTEM AND PROCESS

(71) Applicant: SHELL OIL COMPANY, Houston, TX (US)

(72) Inventors: Jesse Raymond Black, Houston, TX (US); Gregory John Ward, Houston, TX (US); Roel Guillaume Hubertus Leonardus Bastings, Amsterdam (NL); David Allen Van Kleeck, Sugar Land, TX (US); Wayne Errol Evans, Richmond, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 16/061,758

(22) PCT Filed: Dec. 13, 2016

(86) PCT No.: PCT/EP2016/080744
§ 371 (c)(1),
(2) Date: Jun. 13, 2018

(87) PCT Pub. No.: WO2017/102694
PCT Pub. Date: Jun. 22, 2017

(65) Prior Publication Data
US 2018/0369773 A1      Dec. 27, 2018

(30) Foreign Application Priority Data

Dec. 15, 2015   (EP) .................................. 15200254

(51) Int. Cl.
*B01J 8/04*         (2006.01)
*C07D 301/32*    (2006.01)

(52) U.S. Cl.
CPC ........... *B01J 8/0419* (2013.01); *B01J 8/0457* (2013.01); *B01J 8/0492* (2013.01); *B01J 8/0496* (2013.01);
(Continued)

(58) Field of Classification Search
CPC ...... B01J 8/0419; B01J 8/0457; B01J 8/0492; B01J 8/0496; C07D 301/32
See application file for complete search history.

(56) References Cited

U.S. PATENT DOCUMENTS

| 2,289,063 A | | 7/1942 | Ocon et al. | |
|---|---|---|---|---|
| 3,573,201 A | * | 3/1971 | Annesser | ............... C10G 45/02 208/251 H |

(Continued)

FOREIGN PATENT DOCUMENTS

| CN | 1282328 A | 1/2001 |
|---|---|---|
| CN | 103025852 A | 4/2013 |

(Continued)

OTHER PUBLICATIONS

International Search Report and Written Opinion received for PCT Patent Application No. PCT/EP2016/080744, dated Mar. 14, 2017, 12 pages.

(Continued)

*Primary Examiner* — Lessanework Seifu

(57) ABSTRACT

The invention provides a reaction system for the production of ethylene carbonate and/or ethylene glycol. The reaction system having a guard bed system upstream of a catalytic EO reactor. The guard bed system having a feed line supplying a gaseous feed and an effluent line configured to remove the treated gaseous feed. The guard bed system has two or more guard bed vessels arranged in series in sequential order, each having an inlet, a bed of guard bed material and an outlet. The inlet of each guard bed vessel is attached by means of valves to both the feed line and the outlet of the guard bed vessel preceding it in sequential order. The outlet of each guard bed vessel is attached by means of valves to both the effluent line and to the inlet of the guard bed vessel following it in sequential order.

7 Claims, 3 Drawing Sheets

(52) U.S. Cl.
CPC ... *C07D 301/32* (2013.01); *B01J 2208/00176* (2013.01); *B01J 2219/0004* (2013.01)

(56) References Cited

U.S. PATENT DOCUMENTS

| | | |
|---|---|---|
| 4,048,096 A | 9/1977 | Bissot |
| 4,761,394 A | 8/1988 | Lauritzen |
| 4,766,105 A | 8/1988 | Lauritzen |
| 4,789,528 A | 12/1988 | Owen et al. |
| 5,179,057 A | 1/1993 | Bartley |
| 5,189,004 A | 2/1993 | Bartley |
| 5,380,697 A | 1/1995 | Matusz et al. |
| 5,739,075 A | 4/1998 | Matusz |
| 6,040,467 A | 3/2000 | Papavassiliou et al. |
| 6,368,998 B1 | 4/2002 | Lockemeyer |
| 6,656,874 B2 | 12/2003 | Lockemeyer |
| 7,030,056 B2 | 4/2006 | Birke et al. |
| 7,193,094 B2 | 3/2007 | Chipman et al. |
| 7,425,647 B2 | 9/2008 | Lemanski et al. |
| 8,193,374 B2 * | 6/2012 | Evans .............. B01D 53/02 549/230 |
| 8,546,592 B2 | 10/2013 | Evans et al. |
| 8,845,975 B2 | 9/2014 | Henstock et al. |
| 8,921,586 B2 | 12/2014 | Matusz |
| 8,932,979 B2 | 1/2015 | Matusz et al. |
| 2003/0204101 A1 | 10/2003 | Jewson et al. |
| 2006/0070918 A1 | 4/2006 | Seapan et al. |
| 2007/0173655 A1 * | 7/2007 | Grey .............. B01J 23/6484 549/533 |
| 2008/0281118 A1 | 11/2008 | Matusz |
| 2009/0050535 A1 | 2/2009 | Evans |
| 2009/0270640 A1 | 10/2009 | Maurer et al. |
| 2009/0292132 A1 | 11/2009 | Evans |
| 2011/0034710 A1 | 2/2011 | Matusz |
| 2014/0001089 A1 * | 1/2014 | Bazer-Bachi .......... C10G 65/04 208/57 |
| 2017/0291119 A1 | 10/2017 | Wilkinson et al. |

FOREIGN PATENT DOCUMENTS

| | | |
|---|---|---|
| CN | 103502397 A | 1/2014 |
| DE | 202012012866 U1 | 2/2014 |
| EP | 0776890 A2 | 6/1997 |
| EP | 2279182 A1 | 2/2011 |
| GB | 2107712 A | 5/1983 |
| WO | 9908790 A1 | 2/1999 |
| WO | 9908791 A1 | 2/1999 |
| WO | 2008144402 A2 | 11/2008 |
| WO | 2009021830 A1 | 2/2009 |
| WO | 2009140319 A1 | 11/2009 |
| WO | 2012071052 A1 | 5/2012 |
| WO | 2016001348 A1 | 1/2016 |
| WO | 2017102694 A1 | 6/2017 |
| WO | 2017102698 A1 | 6/2017 |
| WO | 2017102701 A1 | 6/2017 |

OTHER PUBLICATIONS

International Search Report and Written Opinion received for PCT Patent Application No. PCT/EP2016/080749, dated Feb. 17, 2017, 8 pages.
International Search Report and Written Opinion received for PCT Patent Application No. PCT/EP2016/080752, dated Apr. 4, 2017, 9 pages.
International Search Report and Written Opinion received for PCT Patent Application No. PCT/EP2016/080759, dated Apr. 4, 2017, 9 pages.
Evans et al., "Industrial Epoxidation Processes", Industrial Epoxidation Processes, Encyclopedia of Catalysis (Wiley-Interscience), 2003, vol. 3, pp. 246-264.
Brunauer et al., "Adsorption of Gases in MultiMolecular Layers", Journal of American Chemical Society, Feb. 1938, vol. 60, Issue No. 2, pp. 309-319.
Kirk-Othmer, Encyclopedia of Chemical Technology, 4th Edition, vol. 9, pp. 915-959.

* cited by examiner

GUARD BED SYSTEM AND PROCESS

CROSS REFERENCE TO RELATED APPLICATIONS

This is a national stage application of International application No. PCT/EP2016/080744, filed 13 Dec. 2016, which claims benefit of priority of European application No. 15200254.9, filed 15 Dec. 2015.

FIELD OF THE INVENTION

The present invention relates to a guard bed system and a process for operating said system for use upstream of an ethylene oxide reactor.

BACKGROUND OF THE INVENTION

Monoethylene glycol is used as a raw material in the manufacture of polyester fibres, polyethylene terephthalate (PET) plastics and resins. It is also incorporated into automobile antifreeze liquids.

Monoethylene glycol is typically prepared from ethylene oxide, which is in turn prepared from ethylene. Ethylene and oxygen are passed over a silver oxide catalyst, typically at pressures of 10-30 bar and temperatures of 200-300° C., producing a product stream comprising ethylene oxide, carbon dioxide, ethylene, oxygen and water. The amount of ethylene oxide in the product stream is usually between about 0.5 and 10 weight percent. The product stream is supplied to an ethylene oxide absorber and the ethylene oxide is absorbed by a re-circulating solvent stream containing water. The ethylene oxide-depleted stream is partially or entirely supplied to a carbon dioxide absorption column wherein the carbon dioxide is at least partially absorbed by a re-circulating absorbent stream. Gases that are not absorbed by the re-circulating absorbent stream are recombined with any gases bypassing the carbon dioxide absorption column and are recycled to the ethylene oxide reactor.

The solvent stream leaving the ethylene oxide absorber is referred to as fat absorbent. The fat absorbent is supplied to an ethylene oxide stripper, wherein ethylene oxide is removed from the fat absorbent as a vapour stream. The ethylene oxide-depleted solvent stream is referred to as lean absorbent and is recirculated to the ethylene oxide absorber to absorb further ethylene oxide.

The ethylene oxide obtained from the ethylene oxide stripper can be purified for storage and sale or can be further reacted to provide ethylene glycol. In one well-known process, ethylene oxide is reacted with a large excess of water in a non-catalytic process. This reaction typically produces a glycol product stream consisting of almost 90 weight percent monoethylene glycol, the remainder being predominantly diethylene glycol, some triethylene glycol and a small amount of higher homologues. In another well-known process, ethylene oxide is reacted with carbon dioxide in the presence of a catalyst to produce ethylene carbonate. The ethylene carbonate is subsequently hydrolysed to provide ethylene glycol. Reaction via ethylene carbonate significantly improves the selectivity of ethylene oxide conversion to monoethylene glycol.

Efforts have been made to simplify the process for obtaining ethylene glycol from ethylene, reducing the equipment that is required and reducing the energy consumption. GB 2107712 describes a process for preparing monoethylene glycol wherein the gases from the ethylene oxide reactor are supplied directly to a reactor wherein ethylene oxide is converted to ethylene carbonate or to a mixture of ethylene glycol and ethylene carbonate.

EP 0776890 describes a process wherein the gases from the ethylene oxide reactor are supplied to an absorber, wherein the absorbing solution mainly contains ethylene carbonate and ethylene glycol. The ethylene oxide in the absorbing solution is supplied to a carboxylation reactor and allowed to react with carbon dioxide in the presence of a carboxylation catalyst. The ethylene carbonate in the absorbing solution is subsequently supplied, with the addition of water, to a hydrolysis reactor and subjected to hydrolysis in the presence of a hydrolysis catalyst.

EP 2178815 describes a reactive absorption process for preparing monoethylene glycol, wherein the gases from the ethylene oxide reactor are supplied to an absorber and the ethylene oxide is contacted with lean absorbent comprising at least 20 wt % water in the presence of one or more catalysts that promote carboxylation and hydrolysis and the majority of the ethylene oxide is converted to ethylene carbonate or ethylene glycol in the absorber.

In each of these cases, a gas stream containing gases that are not absorbed by the recirculating absorbent stream will be produced from the EO absorber or reactive absorber. This gas stream is treated in a carbon dioxide absorption column and then recombined with any gases bypassing the carbon dioxide absorption column. The combined gases are then recycled to the ethylene oxide reactor.

When one or more catalysts that promote carboxylation and hydrolysis are present in the absorber, decomposition materials and side products from these catalysts may be present in the fat absorbent stream and/or the gas stream.

The silver-based ethylene oxide (EO) catalysts generally used in an ethylene oxide reactor are susceptible to catalyst poisons, in particular certain halogen-containing materials, such as some iodide-containing impurities and some bromide-containing impurities. Any such catalyst poisons present in the recycled gas stream will, therefore, need to be removed from the stream before it is contacted with the EO catalysts. The use of a purification zone or guard bed upstream of an epoxidation reactor is disclosed in EP 2285795, EP 2279182 and EP 2155375.

The present inventors have found that the sensitivity of EO catalysts to certain catalyst poisons can be higher than previously expected and simple guard bed systems are not suitable to protect the EO catalyst bed in an reliable and economic manner. An optimised design is required to deliver an effective and economic solution. The present inventors have, therefore, sought to provide an improved guard bed system and process for the removal of EO catalyst poisons in the manufacture of alkylene glycol from an alkene.

SUMMARY OF THE INVENTION

Accordingly, the present invention provides a reaction system for the production of ethylene carbonate and/or ethylene glycol, said reaction comprising a guard bed system positioned upstream of a catalytic EO reactor, said guard bed system comprising a feed line supplying a gaseous feed to be treated and an effluent line configured to remove the treated gaseous feed and two or more guard bed vessels arranged in series in sequential order, each guard bed vessel comprising an inlet, a bed of guard bed material and an outlet, wherein the inlet of each guard bed vessel is attached by means of valves to both the feed line and the outlet of the guard bed vessel preceding it in sequential order and wherein the outlet of each guard bed vessel is attached by means of valves to both the effluent line and to the inlet of the guard bed vessel following it in sequential order and wherein the guard bed vessel following the last guard bed vessel in sequential order is the first guard bed vessel in sequential order.

The present invention also provides a process for operating a guard bed system in a reaction system for the production of ethylene carbonate and/or ethylene glycol as disclosed herein, said process comprising the steps of:
(i) supplying a gaseous feed via a feed line;
(ii) feeding said gaseous feed through two or more guard bed vessels arranged in series, wherein each guard bed vessel comprises a bed of guard bed material capable of removing impurities from the gaseous feed;
(iii) contacting the gaseous feed with the guard bed material in each of the two or more guard bed vessels thereby removing impurities from the gaseous feed;
(iv) removing a treated gaseous feed from the final guard bed vessel in series;
(v) after a period of time, removing the first guard bed vessel from the flow of the gaseous feed and allowing the gaseous feed to continue to flow through the second and any subsequent guard bed vessels;
(vi) refreshing the guard bed material present in the first guard bed vessel; and
(vii) restoring flow of the gaseous feed through the first guard bed vessel such that it is the last guard bed vessel in series to be contacted with the gaseous feed.

DETAILED DESCRIPTION OF THE INVENTION

Figure 1:
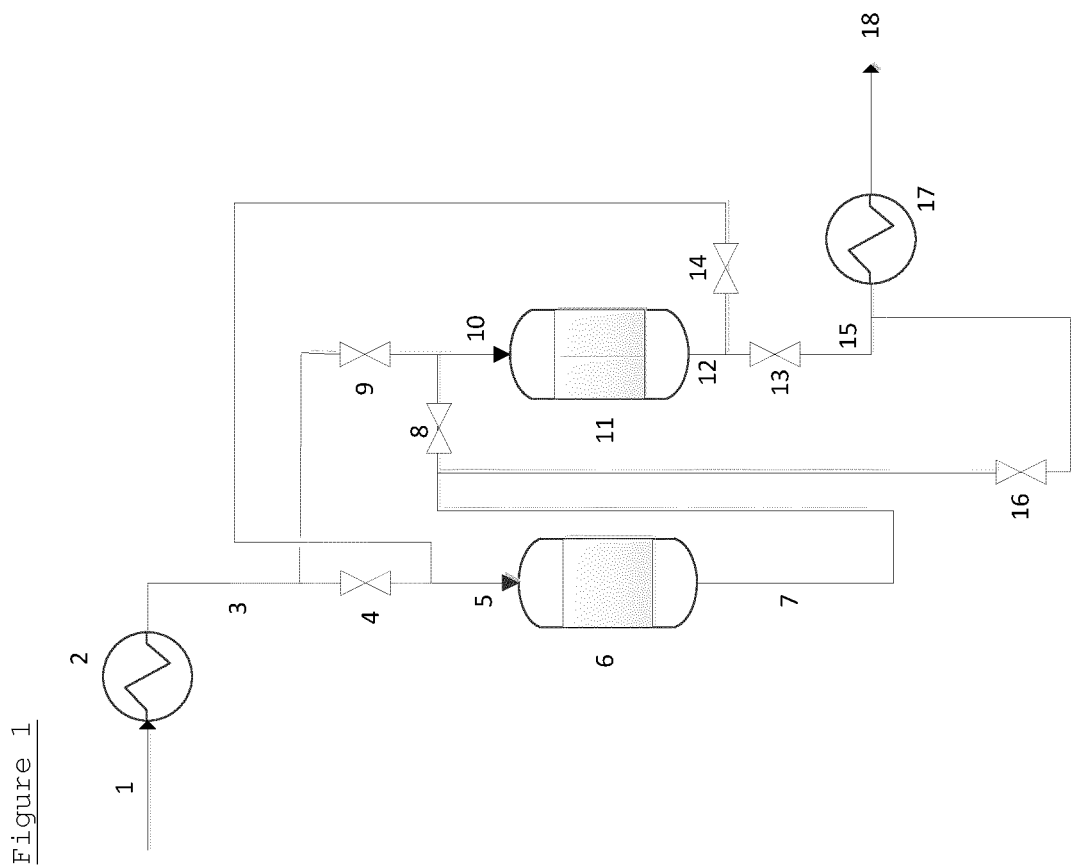
FIGS. 1 to 3 are schematic diagrams showing exemplary, but non-limiting embodiments of the invention.

The present invention provides a guard bed system and a process for operating said system for use upstream of an ethylene oxide reactor.

In an ethylene oxide reactor, ethylene is reacted with oxygen in the presence of a catalyst to form ethylene oxide. In such a reaction, the oxygen may be supplied as oxygen or as air, but is preferably supplied as oxygen. Ballast gas, for example methane or nitrogen, is typically supplied to allow operation at high oxygen levels without causing a flammable mixture. Moderator, e.g. monochloroethane, vinyl chloride or dichloroethane, may be supplied for ethylene oxide catalyst performance control. The alkene, oxygen, ballast gas and moderator are preferably supplied to recycle gas that is supplied to the ethylene oxide reactor from an ethylene oxide absorber (preferably via a carbon dioxide absorption column).

The ethylene oxide reactor is typically a multitubular, fixed bed reactor. The catalyst is preferably finely dispersed silver and optionally promoter metals on a support material, for example, alumina. The reaction is preferably carried out at pressures of greater than 1 MPa and less than 3 MPa and temperatures of greater than 200° C. and less than 300° C. The gas composition from the ethylene oxide reactor is preferably cooled in one or more coolers, preferably with generation of steam at one or more temperature levels.

The gas composition is then passed to an ethylene oxide absorber in which it is intimately contacted with lean absorbent. The lean absorbent comprises at least 20 wt % water. Preferably, the lean absorbent also comprises ethylene carbonate and/or ethylene glycol. At least a portion of, and preferably substantially all of, the ethylene oxide in the gas composition is absorbed into the lean absorbent. Preferably, the gas composition is intimately contacted with the lean absorbent in the presence of one of more catalysts that promote carboxylation and hydrolysis. Suitably, the absorber may be the sort of reactive absorber described in EP 2178815 or in co-pending application EP 14186273.0.

In one embodiment of the invention, the one or more catalysts that promote carboxylation and hydrolysis is/are homogeneous, and the lean absorbent contains the one or more catalysts.

Homogeneous catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenyl-propylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. Preferred homogeneous catalysts that are known to promote carboxylation include alkali metal iodides such as potassium iodide and halogenated organic phosphonium or ammonium salts such as tributylmethylphosphonium iodide, tetrabutylphosphonium iodide, triphenylmethylphosphonium iodide and tributylmethylammonium iodide.

Homogeneous catalysts that are known to promote hydrolysis include basic alkali metal salts such as potassium carbonate, potassium hydroxide and potassium bicarbonate, or alkali metal metalates such as potassium molybdate.

Preferred homogeneous catalyst systems include a combination of potassium iodide and potassium carbonate, and a combination of potassium iodide and potassium molybdate.

In another embodiment of the invention, the one or more catalysts that promote carboxylation and hydrolysis is/are heterogeneous and the heterogeneous catalyst(s) are contained in vertically stacked trays. Heterogeneous catalysts that promote carboxylation include quaternary ammonium and quaternary phosphonium halides immobilized on silica, quaternary ammonium and quaternary phosphonium halides bound to insoluble polystyrene beads, and metal (e.g. zinc) halides, preferably iodides, immobilised on solid supports containing quaternary ammonium or quaternary phosphonium groups, such as ion exchange resins containing quaternary ammonium or quaternary phosphonium groups. Heterogeneous catalysts that promote hydrolysis include metalates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups.

A 'fat absorbent' stream is withdrawn from the alkylene oxide absorber, preferably by withdrawing liquid from the bottom of the alkylene oxide absorber, i.e. below the vertically stacked trays or packing. The fat absorbent stream will contain alkylene carbonate and/or alkylene glycol and any remaining EO, if present, depending on the conditions, set-up and catalyst in the absorber.

Any gases that are not absorbed in the alkylene oxide absorber, including any catalyst decomposition products or side products, are removed from the top of the absorber and are ultimately recycled to the epoxidation reactor. Preferably, at least a portion of the gas to be recycled to the epoxidation reactor will be supplied to a carbon dioxide absorption column, wherein carbon dioxide is at least partially absorbed, before the thus-treated gas is supplied to the epoxidation reactor.

Preferably, the gases are cooled prior to recycle to the epoxidation reactor in order to reduce the water content. This is preferred because the performance of the epoxidation catalyst in the epoxidation reactor may be detrimentally affected by an excess of water. The performance of the guard bed material in the guard bed vessels may also be detrimentally affected by an excess of water. Therefore, it is preferable that the gases are cooled prior to being supplied to the guard bed system. The water removed from the recycle gas stream can optionally be recirculated to the alkylene oxide absorber.

It has been found that when one of more catalysts that promote carboxylation and hydrolysis are present in the absorber and said catalysts comprise one or more iodides or bromides, then gaseous iodide-containing impurities or bromide-containing impurities may be formed which exit the alkylene oxide absorber with the recycle gas stream. These impurities, particularly organic iodide-containing impurities can poison the epoxidation catalyst in the epoxidation reactor, even in minute quantities.

Treating the recycle gas in a guard bed system capable of reducing the quantity of iodide-containing impurities and/or bromide-containing impurities can reduce the quantity of such impurities in the recycle gas and thus protect the performance of the epoxidation catalyst, in particular selectivity, activity, and the duration of time the epoxidation catalyst remains in the epoxidation reactor before having to exchange the catalyst with a fresh epoxidation catalyst.

The present inventors have found that, in particular organic iodide-containing impurities, and more in particular vinyl iodide and alkyl iodides such as ethyl and methyl iodide, in the recycle gas need to be reduced to very low levels in order for the performance of the epoxidation catalyst to remain unaffected by their presence. Preferably, the amount of methyl iodide, ethyl iodide and vinyl iodide in the recycle gas each needs to be reduced to no more than 5 ppbw, more preferably no more than 3 ppbw, even more preferably no more than 2 ppbw, most preferably no more than 1 ppbw.

The present invention therefore provides a guard bed system positioned upstream of a catalytic EO reactor, said guard bed system comprising a feed line supplying a gaseous feed to be treated and an effluent line configured to remove the treated gaseous feed and two or more guard bed vessels arranged in series in sequential order, each guard bed vessel comprising an inlet, a bed of guard bed material and an outlet, wherein the inlet of each guard bed vessel is attached by means of valves to both the feed line and the outlet of the guard bed vessel preceding it in sequential order and wherein the outlet of each guard bed vessel is attached by means of valves to both the effluent line and to the inlet of the guard bed vessel following it in sequential order and wherein the guard bed vessel following the last guard bed vessel in sequential order is the first guard bed vessel in sequential order.

Preferably, the gaseous feed to be treated is the recycle gas from an EO absorber. More preferably, the gaseous feed to be treated is recycle gas from an EO absorber that has yet to be treated in a carbon dioxide absorption column. Positioning the guard bed system at this stage in the process may have the added advantage of protecting the $CO_2$ absorber from any potential effects that may be caused by the impurities that are removed by the guard bed system.

The feed line, optionally, contains one or more heating or cooling devices, such as heat exchangers, in order to alter the temperature of the gaseous feed to be optimal for the guard bed system.

The guard bed system comprises two or more guard bed vessels arranged in sequential order. In one embodiment of the invention it is preferred that the guard bed system comprises more than two, for example 3 or 4, guard bed vessels arranged in series in sequential order.

By sequential order herein is meant that the first guard bed vessel is followed in series by the second guard bed vessel; the second guard bed vessel is followed by the third guard bed vessel, if present; and the third guard bed vessel is followed by the fourth guard bed vessel, if present, etc. The first guard bed vessel is considered to occur in sequential order after the last guard bed vessel.

Each guard bed vessel comprises a bed of guard bed material. Suitable guard bed material is selected from any material that is capable of absorbing material, particularly organic iodide-containing impurities, that is detrimental to the EO catalyst. Preferred materials include those described in EP 2285795 and EP 2155375. It is preferred that all guard bed vessels within a single guard bed system contain the same guard bed material.

Each guard bed vessel comprises an inlet, which is attached by means of valves to both the feed line and the outlet of the guard bed vessel preceding it in sequential order. At any one time, the valves will allow feed from either the feed line or from the guard bed vessel preceding it in sequential order.

Each guard bed vessel comprises an outlet, which is attached by means of valves to both the effluent line and to the inlet of the guard bed vessel following it in sequential order. At any one time, the valves will allow feed to either the effluent line or to the guard bed vessel following it in sequential order.

The valves used in each guard bed system may be any suitable type of valve known to the skilled person. Such valves include, but are not limited to single valves, double valves and double valves in a block and bleed set-up.

The guard bed system comprises an effluent line configured to remove the treated gaseous feed from the system and supply it, directly or indirectly, to the EO reactor. The effluent line, optionally, contains one or more heating or cooling devices, such as heat exchangers, in order to alter the temperature of the gaseous feed to be optimal for the EO reactor or any further treatment of the gaseous feed prior to it being provided to the EO reactor.

In one embodiment of the invention, a guard bed system of the invention may be preceded or followed by a further guard bed device. Such a guard bed device may be of a standard set up known in the art, such as a simple, single bed, guard bed vessel or two such guard beds arranged in parallel to allow the feed to be switched between the two. In this embodiment, the further guard bed device may contain the same or different guard bed material as the guard bed system of the present invention. However in a preferred embodiment of the invention, two or more guard bed systems according to the present invention may be arranged in series, upstream of the EO reactor. In this embodiment the effluent line of the first guard bed system supplies the feed line of the second guard bed system. One or more heating or cooling devices, such as heat exchangers, may be provided in the feed line and/or the effluent line of the first guard bed system and/or in the feed line and/or in the effluent line of the second guard bed system in order to provide feed at an optimal temperature or cool down the effluent. Also, in this embodiment, the guard bed material contained within each guard bed system may be the same or different. Preferably, it is different. The number of guard beds contained within each guard bed system may also be the same or different. Further, the conditions under which the gas is treated in each guard bed system may also be the same or different, depending on the guard bed material contained therein or impurity that should be removed.

Suitably, the treated gaseous feed from the guard bed system(s) of the present invention is supplied to the EO reactor after at least a portion of said feed has been supplied to and treated in a carbon dioxide absorption column.

The present invention also provides a process for operating a guard bed system positioned upstream of a catalytic EO reactor, said process comprising the steps of:
(i) supplying a gaseous feed via a feed line;
(ii) feeding said gaseous feed through two or more guard bed vessels arranged in series, wherein each guard bed vessel comprises a bed of guard bed material capable of removing impurities from the gaseous feed;
(iii) contacting the gaseous feed with the guard bed material in each of the two or more guard bed vessels thereby removing impurities from the gaseous feed;
(iv) removing a treated gaseous feed from the final guard bed vessel in series;
(v) after a period of time, removing the first guard bed vessel from the flow of the gaseous feed and allowing the gaseous feed to continue to flow through the second and any subsequent guard bed vessels;
(vi) refreshing the guard bed material present in the first guard bed vessel; and
(vii) restoring flow of the gaseous feed through the first guard bed vessel such that it is the last guard bed vessel in series to be contacted with the gaseous feed.

As indicated above, the gaseous feed to be treated is the recycle gas from an EO absorber. Preferably, said recycle gas from an EO absorber has yet to be treated in a carbon dioxide absorption column. Preferably, at least a portion of the gas to be recycled to the epoxidation reactor will be supplied to a carbon dioxide absorption column, wherein carbon dioxide is at least partially absorbed, before the thus-treated gas is supplied to the epoxidation reactor and after the gaseous feed has been treated in the guard bed system(s).

The actual content of the gaseous feed will vary depending on the conditions used in the rest of the ethylene oxide, ethylene carbonate or ethylene glycol process.

Within each guard bed system, the gaseous feed passes through each of the two or more guard bed vessels in series and is contacted with the guard bed material in each guard bed vessel whereby impurities are removed. Depending on the impurities content of the gaseous feed, impurities will be removed in the first guard bed vessel and, possibly, the second guard bed vessel and any later guard bed vessels. A treated gaseous feed will be removed from the final guard bed vessel in series. Said treated gaseous feed will have a reduced level of impurities.

In one preferred embodiment, the guard bed material is a silver on alumina-based material. In this embodiment, the guard bed vessels in the guard bed system are preferably operated at a temperature of at least 100° C., more preferably at least 115° C., most preferably at least 120° C. In this embodiment, the guard beds are preferably operated at a temperature of at most 145° C., more preferably at most 140° C., most preferably at most 135° C.

In another preferred embodiment, the guard bed material is a palladium/gold based material, preferably supported on silica. In this embodiment, the guard bed vessels in the guard bed system are preferably operated at a temperature of at least 65° C., more preferably at least 70° C., most preferably at least 83° C. In this embodiment, the guard bed vessels are preferably operated at a temperature of at most 95° C., more preferably at most 90° C., most preferably at most 87° C.

Each bed of guard bed material may be contained within the guard bed vessel in any suitable system. Preferred systems include an axial fixed bed, wherein the gas to be treated is contacted with the bed of guard bed material as an axial flow, and a radial fixed bed, wherein the gas to be treated is supplied from the inlet to the outside of the fixed bed and passes through the fixed bed to the centre of the guard bed vessel and then to the outlet. A radial fixed bed is preferred. Such a bed generally will have a lower pressure drop.

In any embodiment, the pressure in each guard bed system will be determined by the pressure of the gas loop in the overall system. A preferable operating pressure is in the range of from 1 to 4 MPa (gauge). A more preferable operating pressure is in the range of from 2 to 3 MPa (gauge).

As indicated above, a guard bed system according to the present invention may be preceded or followed by a further guard bed device. Such a guard bed device may be of a standard set up known in the art, such as a simple, single bed, guard bed vessel or two such guard beds arranged in parallel to allow the feed to be switched between the two. However, preferably, two or more guard bed systems according to the present invention may be operated in series. In this embodiment, each of the guard bed systems will be operated according to the process of the present invention. Each of the guard bed systems will preferably contain a different guard bed material and will preferably be operated at a temperature and pressure to suit that guard bed material. The gaseous feed may, therefore, be heated or cooled before being supplied to each guard bed system.

In a particularly preferred embodiment of the invention, two or more guard bed systems are operated in series. In this embodiment, each guard bed system will preferably contain a different guard bed material in its guard bed vessels. More preferably, the first guard bed system in series, comprising two or more, preferably more than two guard bed vessels, will contain a silver on alumina-based material as the guard bed material. Also more preferably, the second guard bed system in series, comprising two or more, preferably two guard bed vessels, will contain a palladium/gold based material, preferably supported on silica, as guard bed material. Suitable operating conditions for such systems are indicated above.

After a period of time, the first guard bed vessel in the guard bed system is removed from the flow of the gaseous feed. In order to determine the appropriate period of time, it will be necessary to monitor the level of impurities in the gaseous feed as it leaves and enters each guard bed vessel. Once the amount of impurities in the gaseous feed leaving the first guard bed vessel in series reaches a certain level, for example a level indicating that the guard bed material in the first guard bed vessel is at least 60%, preferably at least 70%, more preferably at least 80%, most preferably at least 90% exhausted, the guard bed vessel is removed from the flow of the gaseous feed by operation of valves. The flow of the gaseous feed continues through the second guard bed vessel and any subsequent guard bed vessels.

The guard bed material in the first guard bed vessel is then refreshed. This may be carried out by removing at least a portion of the guard bed material and replacing it with fresh or re-activated guard bed material.

Once the guard bed material in the first guard bed vessel is refreshed, flow of the gaseous feed through said guard bed vessel is restored by operation of valves. However, it is restored such that the first guard bed vessel is now the last guard bed vessel in series to be contacted with the gaseous feed.

After a further period of time, again determined by monitoring of the level of impurities in the gaseous flow, the same steps are applied to the second guard bed vessel in series (which at this stage is contacted with the gaseous feed first). The guard bed vessel is removed from the flow and the guard bed material contained therein is refreshed before flow of the gaseous feed is restored with the second guard bed vessel now the last guard bed vessel in series to be contacted with the gaseous feed.

This process may be repeated with each guard bed vessel in turn to ensure continuous operation and a high level of impurities removal.

A particular advantage of the present invention is that it allows the guard bed system to be operated such that a very high proportion of catalyst poison impurities present in the recycle gas are removed. At the same time, the guard bed system is used in a reliable, efficient and economic manner. The majority of any impurities are removed in the first guard bed vessel in series. However, any impurities that pass through the first guard bed vessel will be removed in the second and any subsequent guard bed vessels. This allows the first guard bed vessel to remain in service until the guard bed material contained therein is almost totally exhausted. The second guard bed vessel containing mainly fresh guard bed material then takes over the main burden of impurity removal while the guard bed material in the first guard bed vessel is replaced.

In a simple guard bed system, containing for example two guard bed vessels in parallel, the first guard vessel would have to be removed from the gas flow and the guard bed material contained therein replaced long before it was totally exhausted to ensure that a high level of impurity removal was maintained. For example, when the guard bed material in such a system is only 50% used up, the amount of iodide-containing impurities passing through the guard bed vessel will have risen to an unacceptable level. The guard bed vessel will then have to be taken out of service and the guard bed material within it replaced. Thus, expensive guard bed material is wasted.

DETAILED DESCRIPTION OF THE DRAWINGS

The invention will now be described in detail with reference to the non-limiting embodiments shown in the Figures.

In FIG. 1 (for convenience, the EO reactor has not been drawn), an initial gaseous feed 1 is provided to feed line 3, which, optionally, contains a heat exchanger 2. The feed line 3, is connected via valves 4 and 9 to the inlets 5 and 10 of a first guard bed vessel 6 and a second guard bed vessel 11 arranged in series in sequential order. The outlet 7 of the first guard bed vessel 6 is connected via valves 8 and 16 to both the inlet 10 of the second guard bed vessel 11 and the effluent line 15. The outlet 12 of the second guard bed vessel 11 is connected via valves 13 and 14 to both the effluent line 15 and the inlet 5 of the first guard bed vessel 6. The effluent line 15 optionally contains a heat exchanger 17 to provide a treated gaseous feed 18 at an optimal temperature.

In use, initially a gaseous feed 1 is provided through feed line 3. Valves 4, 8 and 13 are open and valves 9, 14 and 16 are shut. The gaseous feed, therefore, passes via inlet 5 to the first guard bed vessel 6, wherein it is brought into contact with the guard bed material contained therein at suitable temperature and pressure and impurities are removed. Subsequently, the gaseous feed passes through outlet 7. The gaseous feed then proceeds through inlet 10 into the second guard bed vessel 11, wherein it is brought into contact with the guard bed material contained therein at suitable temperature and pressure and further impurities may be removed. Subsequently, the gas passes to outlet 12. The gaseous feed then passes to effluent line 15 to provide treated gaseous feed 18, optionally via a heat exchanger 17.

After a period of time determined by the levels of impurities at the outlets of the guard bed vessels, valves 4 and 8 are closed and valve 9 is open. The gaseous feed stream passes only through the second guard bed vessel 11 and the first guard bed vessel is removed from the flow of the gaseous feed. The guard bed material in the first guard bed vessel 6 is refreshed. Valve 13 is then closed and valves 14 and 16 are opened. Flow of the gaseous feed through the first guard bed vessel 6 is restored, but said first guard bed vessel 6 now operates as the last guard bed vessel in series.

Figure 2:
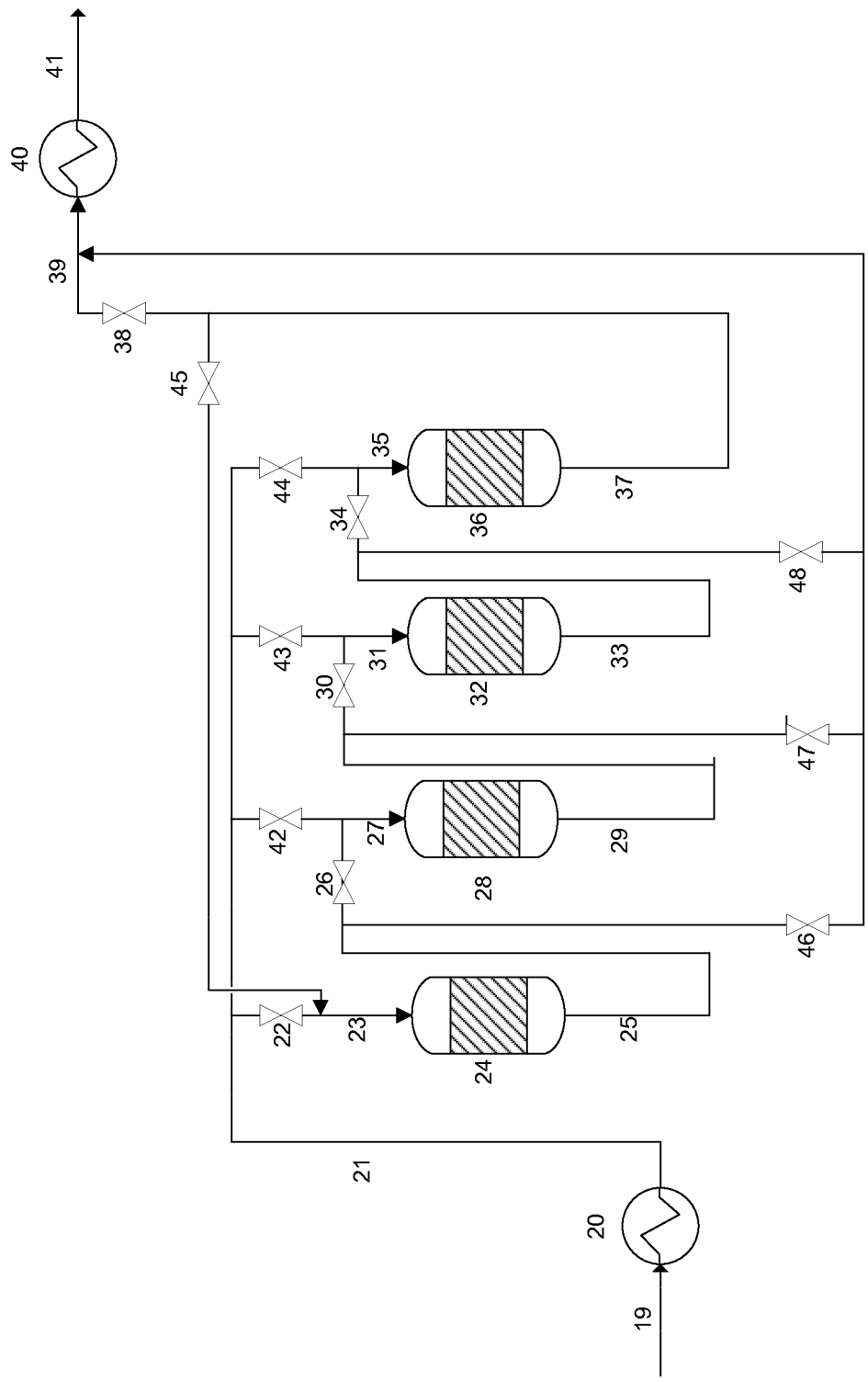

A system containing 4 guard bed vessels is shown in FIG. 2 (for convenience, the EO reactor has not been drawn). In FIG. 2, an initial feed 19 is provided to feed line 21, which, optionally, contains a heat exchanger 20. The feed line 21, is connected via valves 22, 42, 43 and 44 to the inlets 23, 27, 31 and 35 of a first guard bed vessel 24, a second guard bed vessel 28, a third guard bed vessel 32 and a fourth guard bed vessel 36 arranged in series in sequential order. The outlet 25 of the first guard bed vessel 24 is connected via valves 26 and 46 to both the inlet 27 of the second guard bed vessel 28 and the effluent line 39. The outlet 29 of the second guard bed vessel 28 is connected via valves 30 and 47 to both the inlet 31 of the third guard bed vessel 32 and the effluent line 39. The outlet 33 of the third guard bed vessel 32 is connected via valves 34 and 48 to both the inlet 35 of the fourth guard bed vessel 36 and the effluent line 39. The outlet 37 of the fourth guard bed vessel 36 is connected via valves 38 and 45 to both the inlet 23 of the first guard bed vessel 24 and the effluent line 39.

The effluent line 39 optionally contains a heat exchanger 40 to provide a treated gaseous feed 41 at an optimal temperature.

In use, initially a gaseous feed 19 is provided through feed line 21. Valves 22, 26, 30, 34 and 38 are open and valves 42, 43, 44, 45, 46, 47 and 48 are shut. The gaseous feed, therefore, passes via inlet 23 to the first guard bed vessel 24, wherein it is brought into contact with the guard bed material contained therein at suitable temperature and pressure and impurities are removed. Subsequently, the gaseous feed passes through outlet 25. The gaseous feed then proceeds through inlet 27 into the second guard bed vessel 28, wherein it is brought into contact with the guard bed material contained therein at suitable temperature and pressure and further impurities may be removed. Subsequently, the gas passes to outlet 29. The gaseous feed then proceeds through inlet 31 into the third guard bed vessel 32, wherein it is brought into contact with the guard bed material contained therein at suitable temperature and pressure and further impurities may be removed. Subsequently, the gas passes to outlet 33. The gaseous feed then proceeds through inlet 35 into the fourth guard bed vessel 36, wherein it is brought into contact with the guard bed material contained therein at suitable temperature and pressure and further impurities may be removed. Subsequently, the gas passes to outlet 37. The gaseous feed then passes to effluent line 39 to provide treated gaseous feed 41, optionally via a heat exchanger 40.

After a period of time determined by the levels of impurities at the outlets of the guard bed vessels, valves 22 and 26 are closed and valve 42 is open. The gaseous feed stream passes only through the second guard bed vessel 28, the third guard bed vessel 32 and the fourth guard bed vessel 36. The first guard bed vessel 24 is removed from the flow of the gaseous feed. The guard bed material in the first guard bed vessel 24 is refreshed. Valve 38 is then closed and valves 45 and 46 are opened. Flow of the gaseous feed through the first guard bed vessel 24 is restored, but said first guard bed vessel 24 now operates as the last guard bed vessel in series.

After a further period of time determined by the levels of impurities at the outlets of the guard bed vessels, valves 42 and 30 are closed and valve 43 is open. The gaseous feed stream passes only through the third guard bed vessel 32, the fourth guard bed 3 vessel 6 and then the first guard bed vessel 24. The second guard bed vessel 28 is removed from the flow of the gaseous feed. The guard bed material in the second guard bed vessel 28 is refreshed. Valve 46 is then closed and valves 26 and 47 are opened. Flow of the gaseous feed through the second guard bed vessel 28 is restored, but said second guard bed vessel 28 now operates as the last guard bed vessel in series.

The process can then be repeated with the third and fourth guard bed vessels in turn.

Figure 3:
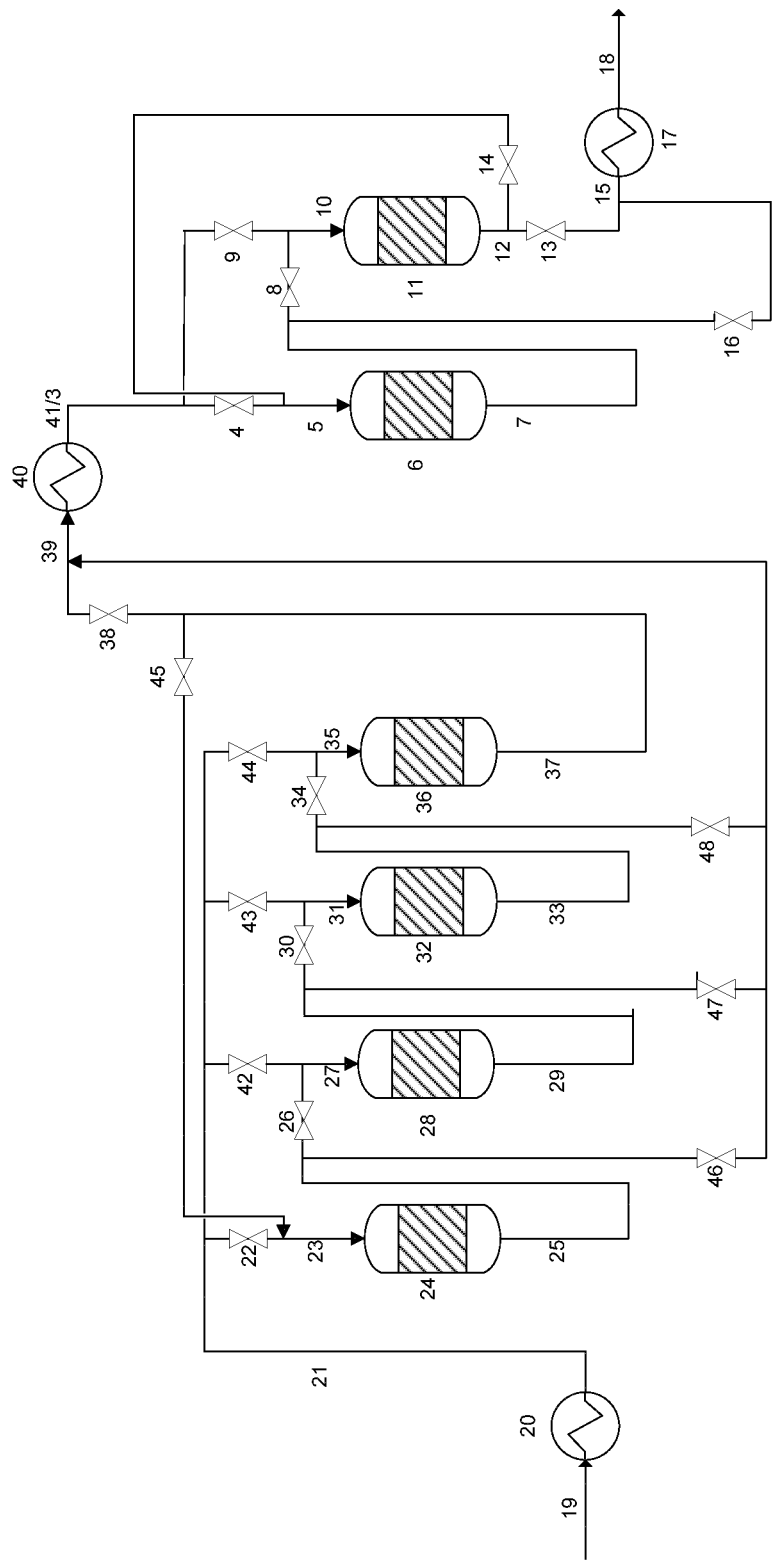

FIG. 3 (for convenience, the EO reactor has not been drawn) shows an embodiment where two guard bed systems, one comprising four guard bed vessels and one comprising two guard bed vessels, are operated in series. Each guard bed system is operated independently of the other and by the processes described above for FIGS. 1 and 2. The treated gaseous feed 41 from a first guard bed system is provided to feed line 3 of the second guard bed system. In this embodiment, heat exchanger 40 can be used to provide the gaseous feed to the second guard bed system at the optimum temperature for that guard bed system.

That which is claimed is:

1. A process for operating a guard bed system in a reaction system for the production of ethylene carbonate and/or ethylene glycol said reaction system comprising a guard bed system positioned upstream of a catalytic EO reactor, said guard bed system comprising a feed line supplying a gaseous feed to be treated and an effluent line configured to remove the treated gaseous feed and two or more guard bed vessels arranged in series in sequential order, each guard bed vessel comprising an inlet, a bed of guard bed material and an outlet, wherein the inlet of each guard bed vessel is attached by means of valves to both the feed line and the outlet of the guard bed vessel preceding it in sequential order and wherein the outlet of each guard bed vessel is attached by means of valves to both the effluent line and to the inlet of the guard bed vessel following it in sequential order and wherein the guard bed vessel following the last guard bed vessel in sequential order is the first guard bed vessel in sequential order, said process comprising the steps of:
 (i) supplying a gaseous feed via a feed line;
 (ii) feeding said gaseous feed through two or more guard bed vessels arranged in series, wherein each guard bed vessel comprises a bed of guard bed material capable of removing impurities from the gaseous feed;
 (iii) contacting the gaseous feed with the guard bed material in each of the two or more guard bed vessels thereby removing impurities from the gaseous feed;
 (iv) removing a treated gaseous feed from the final guard bed vessel in series;
 (v) after a period of time, removing the first guard bed vessel from the flow of the gaseous feed and allowing the gaseous feed to continue to flow through the second and any subsequent guard bed vessels;
 (vi) refreshing the guard bed material present in the first guard bed vessel; and
 (vii) restoring flow of the gaseous feed through the first guard bed vessel such that it is the last guard bed vessel in series to be contacted with the gaseous feed
 wherein the guard bed material contained within the second guard bed system arranged in series comprises palladium and gold, preferably supported on silica.

2. The process according to claim 1, wherein two or more guard bed systems operated by this process are arranged in series and the treated gaseous feed stream removed from the final guard bed vessel in series of the first guard bed system is supplied as the gaseous feed via a feed line to the second guard bed system.

3. The process according to claim 2, wherein the guard bed material contained within the first guard bed system arranged in series comprises silver on alumina.

4. The process of claim 1 wherein the reaction system further comprises an ethylene oxide absorber wherein the gas composition from the catalytic EO reactor is contacted with a lean absorbent in the presence of one or more catalysts that promote carboxylation and hydrolysis to produce a gas stream, at least a portion of which gas stream is passed to the guard bed system of claim 1.

5. The process according to claim 1, wherein each bed of guard bed material is a radial fixed bed.

6. The process according to claim 1, wherein the guard bed system is also upstream of a carbon dioxide absorber, which is upstream of the catalytic EO reactor.

7. The process according to claim 3, wherein the guard bed material contained within the first guard bed system arranged in series comprises silver on alumina and said guard bed system comprises more than two guard bed vessels arranged in series.

* * * * *